(12) United States Patent
Isaacson et al.

(10) Patent No.: US 11,980,727 B2
(45) Date of Patent: May 14, 2024

(54) NEEDLE PROTECTION DEVICE AND RELATED SYSTEMS AND METHODS

(71) Applicant: Becton, Dickinson and Company, Franklin Lakes, NJ (US)

(72) Inventors: S. Ray Isaacson, Layton, UT (US); Marty Stout, South Jordan, UT (US); Austin McKinnon, Herriman, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 13 days.

(21) Appl. No.: 17/337,185

(22) Filed: Jun. 2, 2021

(65) Prior Publication Data

US 2021/0386975 A1    Dec. 16, 2021

Related U.S. Application Data

(60) Provisional application No. 63/037,329, filed on Jun. 10, 2020.

(51) Int. Cl.
*A61M 39/06* (2006.01)
*A61M 25/00* (2006.01)
(Continued)

(52) U.S. Cl.
CPC .... *A61M 25/0631* (2013.01); *A61M 25/0097* (2013.01); *A61M 25/02* (2013.01);
(Continued)

(58) Field of Classification Search
CPC .......... A61M 25/0631; A61M 25/0097; A61M 25/02; A61M 39/06; A61M 2025/0273;
(Continued)

(56) References Cited

U.S. PATENT DOCUMENTS

2002/0026154 A1\* 2/2002 Chang ................ A61M 5/3273
604/198
2009/0292243 A1\* 11/2009 Harding ............ A61M 25/0618
604/110
(Continued)

FOREIGN PATENT DOCUMENTS

AU      2012318627      3/2017
EP       2692389        2/2014

*Primary Examiner* — Brandy S Lee
*Assistant Examiner* — Phoebe Anne Staton
(74) *Attorney, Agent, or Firm* — Kirton McConkie; Whitney Blair; Kevin Stinger

(57) ABSTRACT

A needle protection device may include a hub, a housing disposed within the lumen of the hub, and a needle. The housing may include a tubular portion, which may include two arms coupled thereto. Each of the arms may include a first end coupled to the tubular portion, a second end disposed within the tubular portion, and a bent portion therebetween. The second end of the first arm and the second end of the second arm may form a duckbill valve. A needle may extend through the housing. Withdrawing a sharp distal tip of the needle in a proximal direction beyond the second end of each of the arms may close the duckbill valve and facilitate removal of the housing from the hub. Shielding the sharp distal tip of the needle in this manner may prevent blood spatter and exposure to blood and blood-borne pathogens.

15 Claims, 14 Drawing Sheets

(51) Int. Cl.
*A61M 25/02* (2006.01)
*A61M 25/06* (2006.01)

(52) U.S. Cl.
CPC ..... *A61M 39/06* (2013.01); *A61M 2025/0273* (2013.01); *A61M 2039/0646* (2013.01)

(58) Field of Classification Search
CPC ...... A61M 2039/0646; A61M 25/0606; A61M 25/0618; A61M 25/0084; A61M 25/0075; A61M 25/0625; A61M 25/065; A61M 2210/12; A61M 5/3273; A61M 2005/3247; A61M 5/321
See application file for complete search history.

(56) References Cited

U.S. PATENT DOCUMENTS

| | | |
|---|---|---|
| 2014/0039399 A1 | 2/2014 | Burkholz |
| 2014/0135702 A1 | 5/2014 | Woehr et al. |
| 2018/0200454 A1* | 7/2018 | Haindl ................ A61M 1/1654 |
| 2018/0289932 A1* | 10/2018 | Isaacson ........... A61M 25/0618 |

* cited by examiner

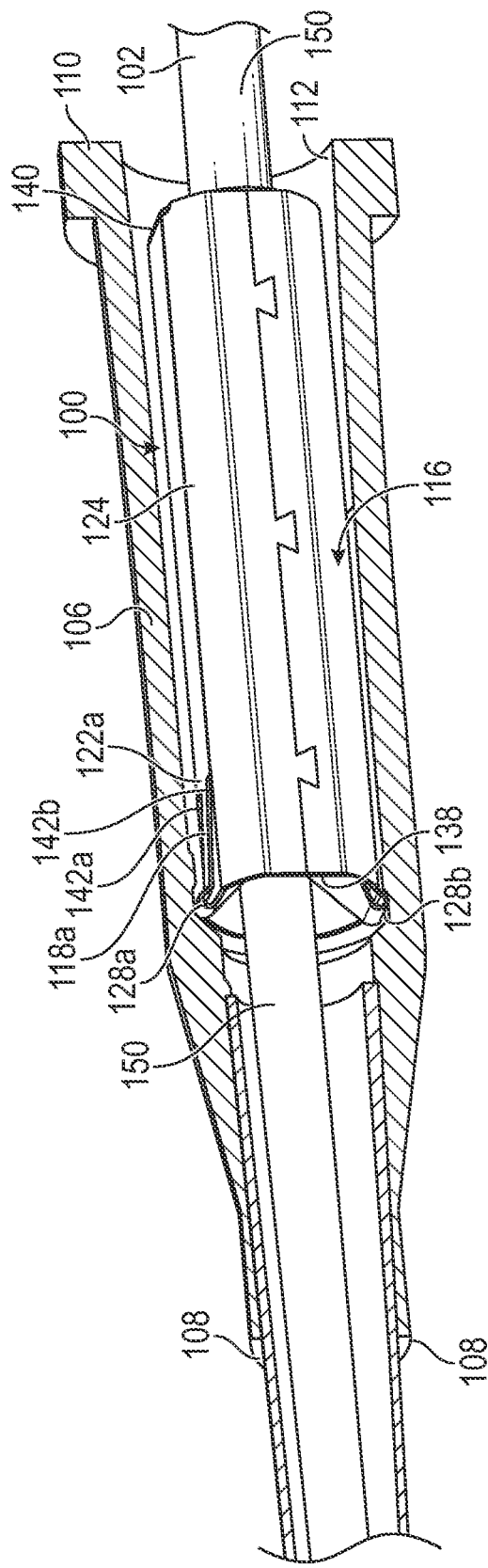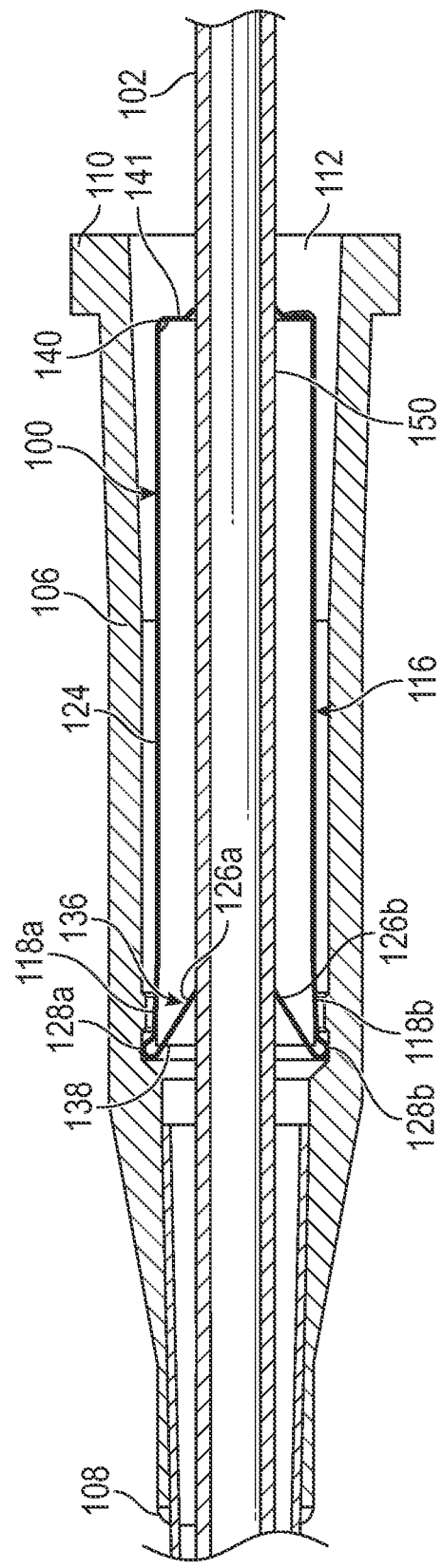

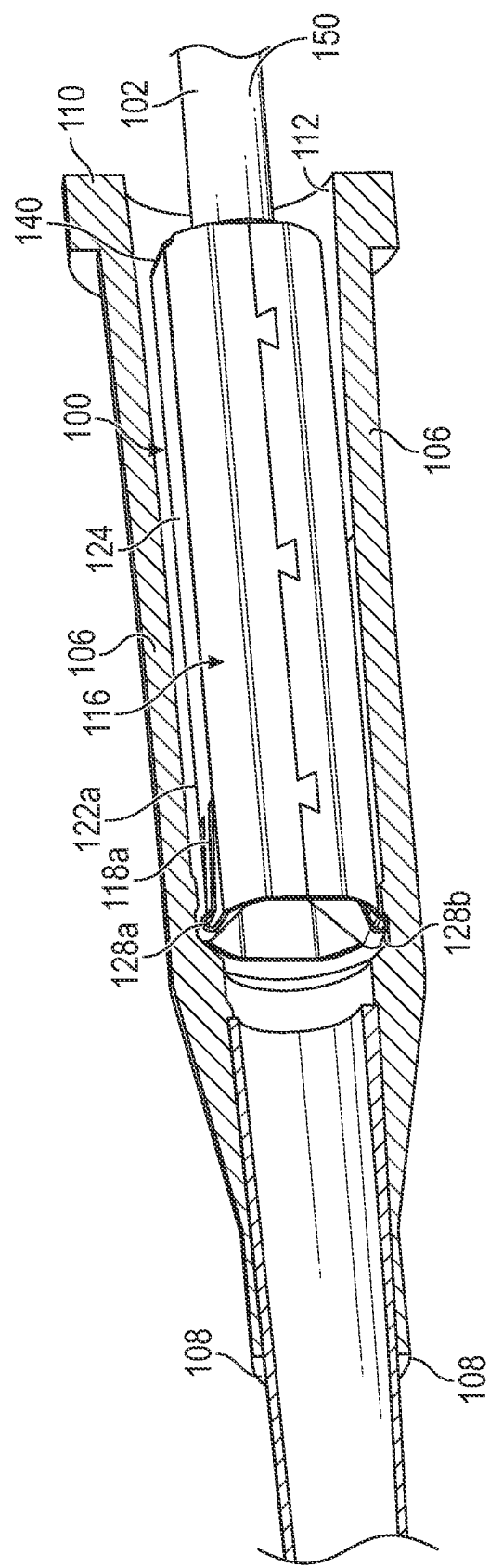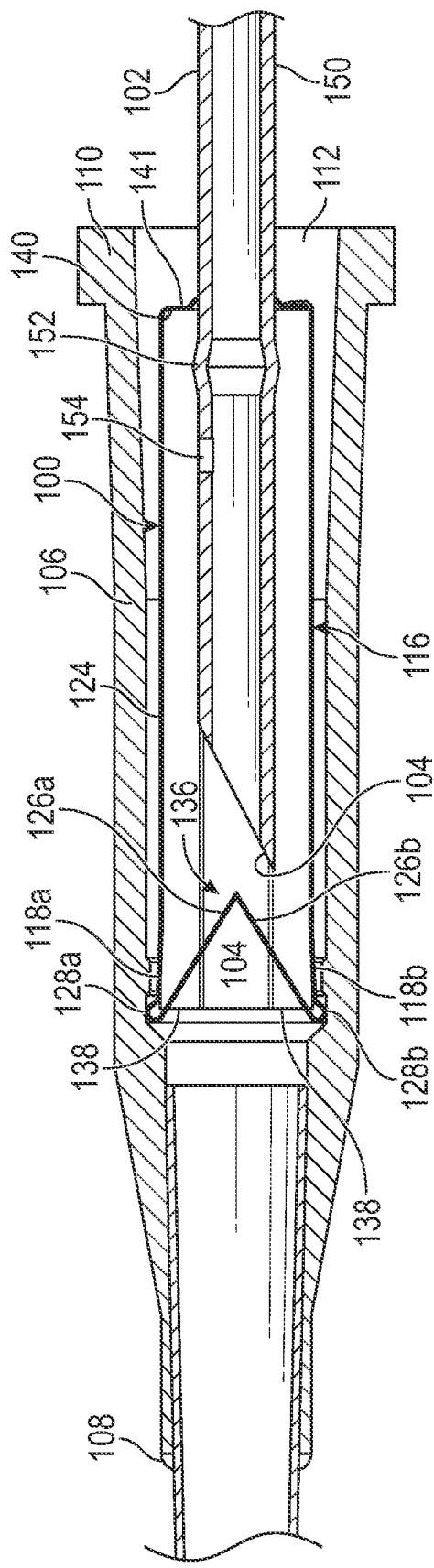

NEEDLE PROTECTION DEVICE AND RELATED SYSTEMS AND METHODS

RELATED APPLICATIONS

This application claims benefit of U.S. Provisional Patent Application No. 63/037,329, filed on Jun. 10, 2020, entitled NEEDLE PROTECTION DEVICE AND RELATED SYSTEMS AND METHODS, which is incorporated herein in its entirety.

BACKGROUND

Intravenous catheters are traditionally used to infuse fluids, such as saline solution, various medicaments, and/or total parenteral nutrition into a patient. Such catheters may also be used to withdraw blood from a patient, and/or monitor various parameters of the patient's vascular system.

To introduce an intravenous catheter into a patient, an over-the-needle peripheral intravenous ("IV") catheter may be mounted over a hollow-bore introducer needle, which may include a sharp distal tip. The inner surface of the catheter may tightly engage the outer surface of the needle to prevent catheter peel back and facilitate insertion of the catheter into a blood vessel. The tip of the introducer needle may extend beyond the distal tip of the catheter to enable insertion of the catheter at a shallow angle through the patient's skin and into the blood vessel.

To verify proper placement of the needle and the catheter in the blood vessel, the clinician may confirm the presence of "flashback" blood in a flashback chamber associated with the catheter and needle assembly. Once proper placement is confirmed, the clinician may then apply pressure to the blood vessel to occlude the vessel, thereby reducing further blood flow through the introducer needle and catheter. The clinician may then withdraw the needle from the catheter to enable continued access to the blood vessel through the catheter. This process of physically manipulating and disassembling the needle and catheter after the catheter has been properly positioned creates substantial risks of accidental needle sticks and exposure to blood and blood-borne pathogens.

Additionally, it has been observed that withdrawing the needle from a catheter assembly may impart energy to parts of the needle. For instance, during withdrawal of the introducer needle, bending forces can be applied (either unintentionally or intentionally) to the needle. The bending forces on the needle may cause blood to splatter or spray from the needle when the needle vibrates and shakes as it becomes free from the catheter assembly and releases stored energy. Accordingly, there is a need in the art for devices, systems, and methods that provide catheter assemblies with increased needle safety.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure generally relates to a needle protection device, as well as to related devices, systems, and methods. A needle protection device in accordance with some embodiments may facilitate securement of the needle protection device within a hub until the needle is withdrawn and a sharp distal tip of the needle is shielded or enclosed for safe disposal. This may reduce a potential for harm arising from contact with sharp edges or exposure to residual blood in the needle. Some embodiments in accordance with the present disclosure may also reduce a risk of premature disarming or removal of the needle protection device.

In some embodiments, an access system may include the hub, the needle protection device, and a needle. In some embodiments, the access system may include a catheter system, and the hub may include a catheter hub. In some embodiments, the access system may include any suitable vascular access system or any suitable cerebral spinal fluid access system. In some embodiments, the hub may include a distal end, a proximal end, and a lumen extending through the distal end and the proximal end. In some embodiments, the needle protection device may include a housing. In some embodiments, the housing may be disposed within the lumen of the hub and, in some embodiments, may be monolithically formed as a single unit.

In some embodiments, the housing may include a tubular portion. In some embodiments, the housing may include a first arm, which may include a first end coupled to the tubular portion, a second end disposed within the tubular portion, and a bent portion disposed between the first end and a second end. In some embodiments, the housing may further include a second arm that may include a first end coupled to the tubular portion, a second end disposed within the tubular portion, and a bent portion disposed between the first end and the second end. In some embodiments, the first end of the first arm and the first end of the second arm may be generally planar and flush with an outer surface of the tubular portion in response to the needle being in a shield position. In some embodiments, the second end of the first arm and the second end of the second arm may form a duckbill valve.

In some embodiments, the needle may extend through the housing and may bias the first arm and the second arm outwardly towards the hub. In some embodiments, the needle may thus facilitate retention of the housing within the hub. In some embodiments, in response to withdrawing the sharp distal tip of the needle in a proximal direction beyond the second end of the first arm and the second end of the second arm, the duckbill valve may close. In some embodiments, in response to withdrawing the sharp distal tip of the needle in a proximal direction beyond the second end of the first arm and the second end of the second arm, the first arm and the second arm may move inwardly to facilitate removal of the housing from the hub.

In some embodiments, the tubular portion of the housing may include a distal end and a proximal end. In some embodiments, each of the first end of the first arm and the first end of the second arm may be formed by slits within the tubular portion. In some embodiments, the slits may extend through the distal end of the tubular portion. In some embodiments, in response to the needle protection device being in a shield position, the tubular portion may be closed except for the slits.

In some embodiments, the needle may include a feature disposed proximal to the sharp distal tip, and the housing may include a proximal opening. In some embodiments, a washer may be coupled to a proximal end of the tubular portion to form the proximal opening. In some embodiments, a diameter of the proximal opening may be less than a diameter of the feature, thereby preventing the sharp distal tip from being withdrawn proximally through the proximal opening.

In some embodiments, the needle may further include a notch providing access to a lumen of the needle. In some embodiments, in response to the sharp distal tip being withdrawn beyond the second end of the first arm and the second end of the second arm and the feature contacting the washer, the notch may be disposed within the tubular portion proximal to the duckbill valve.

In some embodiments, an inner surface of the hub may form the lumen of the hub and may include one or more recesses. In some embodiments, the first arm may include a first interlock protrusion and/or the second arm may include a second interlock protrusion. In some embodiments, in response to the needle extending through the duckbill valve, the first interlock protrusion and/or the second interlock protrusion may be disposed within the recesses. This may facilitate retention of the housing within the hub. In some embodiments, in response to the sharp distal tip being withdrawn beyond the second end of the first arm and the second end of the second arm, the duckbill valve may close. In addition, in some embodiments, in response to the sharp distal tip being withdrawn beyond the second end of the first arm and the second end of the second arm, the first interlock protrusion and the second interlock protrusion may be removed from the recesses, thereby facilitating removal of the housing from the hub.

In some embodiments, the first interlock protrusion may include the first bent portion and/or the second interlock protrusion may include the second bent portion. In other embodiments, the first interlock protrusion may be disposed proximal to the first bent portion, and the second interlock protrusion may be disposed proximal to the second bent portion.

In some embodiments, a first friction pad may be coupled to the first arm and/or a second friction pad may be coupled to the second arm. In some embodiments, the needle may extend through the housing and bias the first arm outwardly towards the hub such that the first friction pad contacts the hub. In some embodiments, the needle may extend through the housing and bias the second arm outwardly towards the hub such that the second friction pad contacts the hub. In some embodiments, in response to the sharp distal tip being withdrawn in the proximal direction beyond the second end of the first arm and the second end of the second arm, the first friction pad and/or the second friction pad may be spaced apart from the hub.

In some embodiments, a friction band may surround the housing. In some embodiments, the needle may extend through the housing and bias the first arm and the second arm outwardly towards the hub such that the friction band contacts the hub. In some embodiments, in response to the sharp distal tip being withdrawn in the proximal direction beyond the second end of the first arm and the second end of the second arm, the friction band may be spaced apart from the hub.

In some embodiments, a housing retention mechanism may include the first friction pad and/or the second friction pad. In some embodiments, the housing retention mechanism may include the friction band. In some embodiments, the housing retention mechanism may include the first interlock protrusion and/or the second interlock protrusion.

In some embodiments, the access system may include a first spring element disposed proximal to the first bent portion and/or a second spring element disposed proximal to the second bent portion. In some embodiments, in response to the needle extending through the housing and biasing the first arm and the second arm outwardly towards the hub, the first spring element may be biased against the second end of the first arm and the second spring element may be biased against the second end of the second arm.

It is to be understood that both the foregoing general description and the following detailed description are examples and explanatory and are not restrictive of embodiments as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 3A is a partial cutaway view of an example access system, illustrating a needle in a ready position and the needle protection device of FIG. 2A, in accordance with some embodiments;

FIG. 3B is a cross-sectional view of the access system of FIG. 3A, illustrating the needle in the ready position, in accordance with some embodiments;

FIG. 3C is a partial cutaway view of the access system of FIG. 3A, illustrating the needle in a shielded position, in accordance with some embodiments;

FIG. 3D is a cross-sectional view of the access system of FIG. 2A, illustrating the needle in the shielded position, in accordance with some embodiments;

DESCRIPTION OF EMBODIMENTS

Figure 1A:
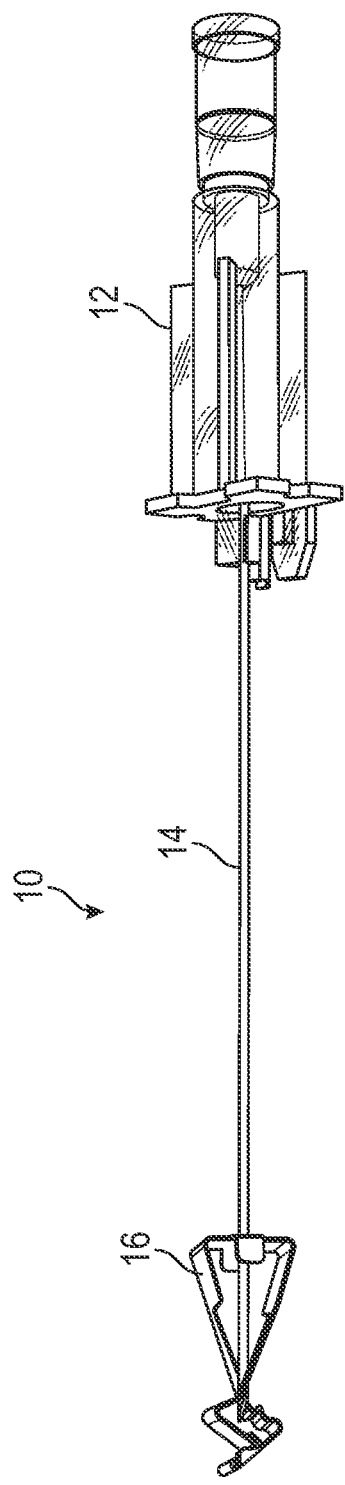
FIG. 1A is an upper perspective view of a prior art needle assembly.
Figure 1B:
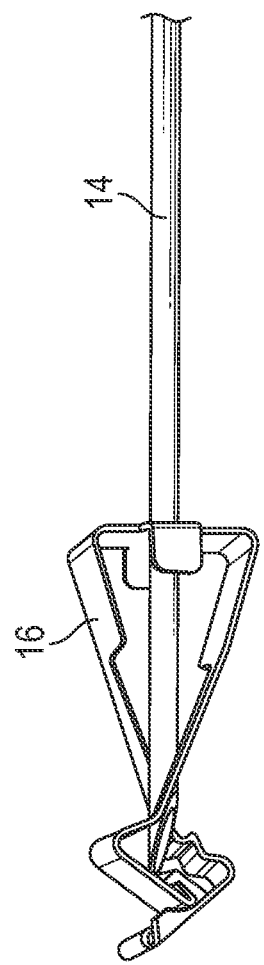
FIG. 1B is an enlarged upper perspective view of a portion of the prior art needle assembly of FIG. 1A.
Figure 2A:
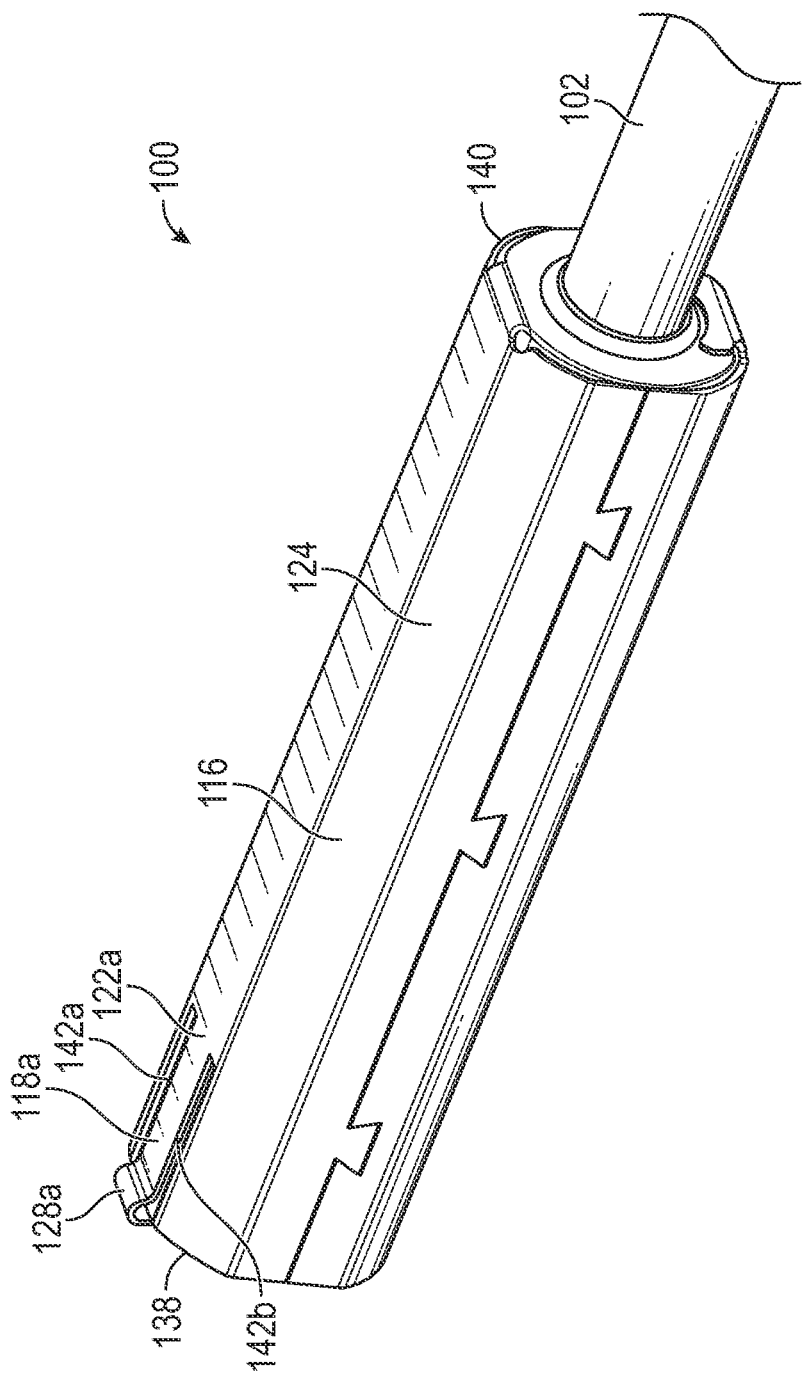
FIG. 2A is an upper perspective view of an example needle protection device, in accordance with some embodiments.
Figure 2B:
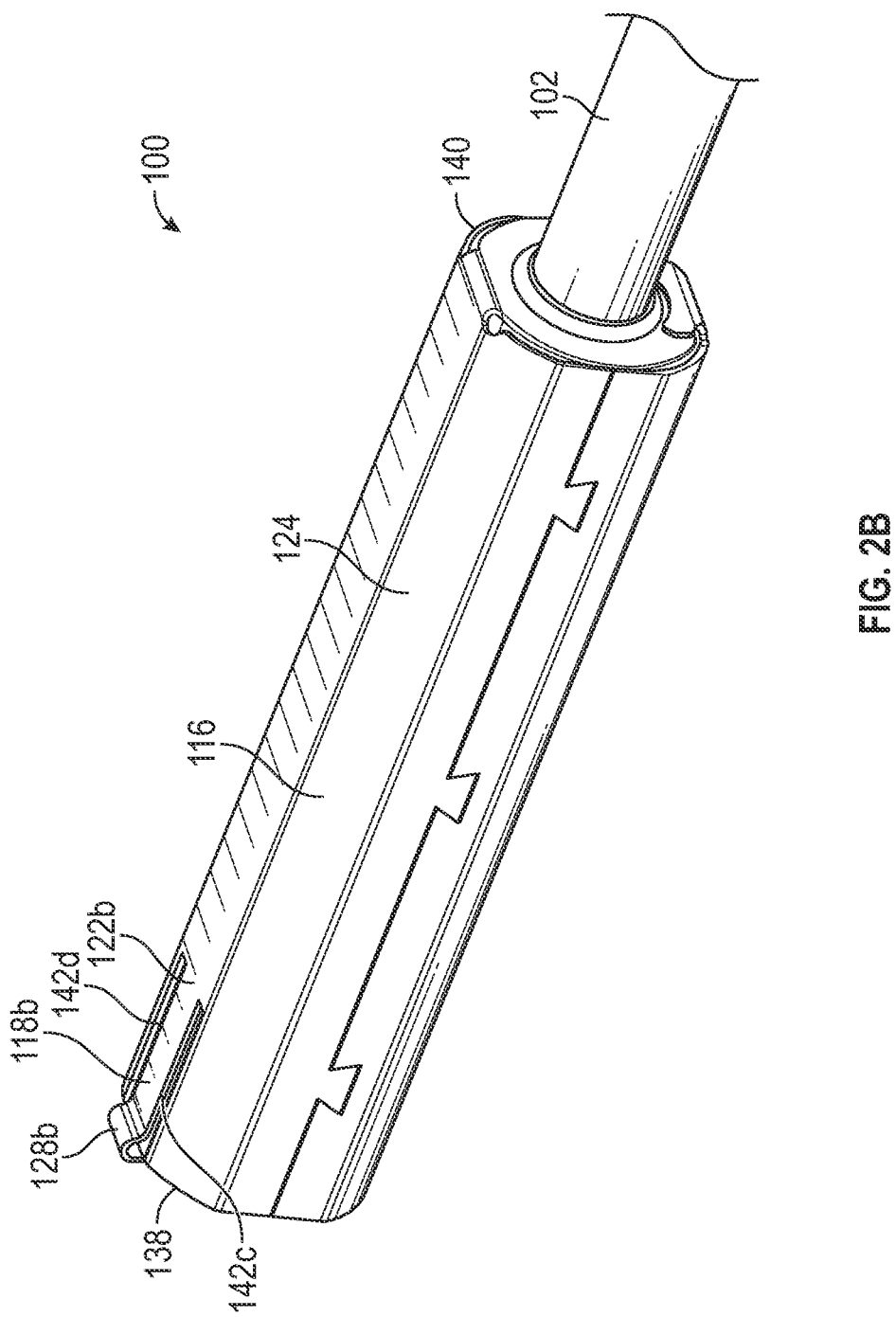
FIG. 2B is a lower perspective view of the needle protection device of FIG. 2A, in accordance with some embodiments.

FIG. 1A illustrates a needle assembly 10 commonly used in the medical field. The needle assembly 10 may include a needle hub 12, a needle 14 extending distally from the needle hub 12, and a spring clip 16. In some embodiments, the needle 14 may include a device used to pierce the skin to acquire intravenous access, such as, for example, an introducer needle. The spring clip 16 is enlarged in FIG. 1B. The needle assembly 10 may be part of an intravenous (IV) catheter system (not illustrated in FIGS. 1A-1B) and may provide several functions. For example, when the needle 14 of the needle assembly 10 is in a ready position for insertion into a vein of a patient, flexible arms of the spring clip 16 may be urged outward and may interfere with a retention feature on an inner surface of a catheter adapter of the IV catheter system, holding the spring clip 16 in place until the needle 14 is withdrawn. The catheter adapter may include a medical device providing fluid communication and mechanical connection between the IV catheter and another vascular access device, such as a needle, a syringe, a blood collection set, an infusion set, or the like.

In response to placement of the IV catheter of the catheter system into the vein of the patient, the needle 14 may be retracted or withdrawn proximally. In response to the needle 14 being withdrawn proximally beyond a distal end of the spring clip 16, the flexible arms may move inwardly, which may first release the interference between the spring clip 16 and the retention feature of the catheter adapter, and then provide a distal barrier for the needle 14, preventing a needle stick injury. Release of the interference between the spring clip 16 and the retention feature may facilitate removal of the needle assembly 10 from the catheter adapter.

The needle assembly 10 and the spring clip 16 may pose several hazards. In some embodiments, the spring clip 16 may be constructed of metal and/or may include one or more sharp edges, which may increase a risk that the patient or a clinician may be cut or scratched by the spring clip 16, particularly when the needle assembly 10 is removed from the catheter adapter. In some instances, the sharp edges of the spring clip 16 may be exposed to blood of the patient, and if the clinician contacts the sharp edges, this could lead to infection by one or more blood borne pathogens. Also, the sharp edges of the spring clip 16 may get caught on clothing, bedding, or another material, which may cause the clip to open, allowing a sharp distal tip of the needle to become exposed. Furthermore, an interior lumen of the needle 14 and/or a notch of the needle 14 may be filled with blood, and the blood may spatter or be ejected from the needle 14 when the needle assembly 10 is removed from the catheter adapter.

Referring now to FIGS. 2A-3D, a needle protection device 100 in accordance with various embodiments may overcome disadvantages of the prior art, as explained in further detail below. In some embodiments, the needle protection device 100 may shield a sharp distal tip 104 of a needle 102 after use to protect against blood spatter and exposure. In some embodiments, the needle protection device 100 may further provide a safety mechanism that remains within a hub 106 until the needle 102 is withdrawn, and automatically encloses the sharp distal tip 104 for safe disposal. In some embodiments, the hub 106 may include a catheter hub or another suitable hub. In some embodiments, an access tube, such as, for example, a catheter, may extend distally from the hub 106. In some embodiments, the catheter may include a peripheral intravenous catheter, a midline catheter, or a peripherally-inserted central catheter.

Advantageously, some embodiments provide the needle protection device 100 that may be monolithically formed as a single unit to reduce exposure to blood and blood-borne pathogens. Some embodiments of the needle protection device 100 may include smooth features to reduce a risk of injury or harm to clinicians from cuts or scratches that may result from contact with sharp edges. Some embodiments of the needle protection device 100 may also provide one or more safety mechanisms which are difficult to manually defeat, and which also resist accidental disabling due to catching on bedding, clothing, or the like.

In some embodiments, the needle protection device 100 may include a housing 116 configured to surround an outer periphery of the needle 102. In some embodiments, the housing 116 may include a cylindrical or tubular portion 124. In some embodiments, the housing 116 may include a substantially rigid, durable and puncture-resistant material such as, for example, metal, plastic, or a composite thereof. In some embodiments, the housing 116 may include sheet metal, such as stainless steel or aluminum. In some embodiments, the sheet metal may include a gauge sufficient to form the housing 116 to include the tubular portion 124, while preventing the needle 102 from puncturing or otherwise compromising the integrity of the housing 116.

In some embodiments, the tubular portion 124 may encircle the needle 102 around a longitudinal axis of the needle 102. In some embodiments, the tubular portion 124 may include two or more pieces molded or joined together along their longitudinal edges to form the tubular portion 124. In some embodiments, the two or more pieces may be joined together by one or more dovetail or other joints. In some embodiments, the housing 116 may be monolithically formed as a single unit. In some embodiments, the housing 116 may be formed from a single sheet of sheet metal.

In some embodiments, the housing 116 may further include a first arm 118a and/or a second arm 118b. In some embodiments, each of the arms 118a,b (which may be referred to herein as "arms 118") may be integrated with or coupled to the tubular portion 124. For example, in some embodiments, each of the arms 118 may be formed by a pair of slits 142a-d disposed in the tubular portion 124 of the housing 116.

In some embodiments, the first arm 118a may include the first end 122a integrated with or coupled to the tubular portion 124, a second end 126a disposed within the tubular portion 124, and a hinged or bent portion 128a therebetween. Likewise, in some embodiments, the second arm 118b may include a first end 122b integrated with or coupled to the tubular portion 124, a second end 126b disposed within the tubular portion 124, and a hinged or bent portion 128b therebetween. The first ends 122a,b may be referred to herein as "first ends 122." The second ends 126a,b may be referred to herein as "second ends 126." In some embodiments, the second end 126a of the first arm 118a and the second end 126b of the second arm 118b may extend into the tubular portion 124 at substantially acute angles and be oriented such that the second ends 126a,b of the arms 118 meet. In some embodiments, the second ends 126a,b may form a duckbill valve 136, which may be one-way. In one embodiment, the duckbill valve 136 may be substantially centered within the tubular portion 124.

In some embodiments, the housing 116 may be configured to allow the needle 102 to slide in a distal direction through a distal end 138 of the tubular portion 124 during assembly. In some embodiments, in response to the needle protection device 100 being in a shield position, the tubular portion 124 may be closed except for the slits 142a-d, which may include narrow spaces. In some embodiments, the slits 142 may each include a cut without a narrow space such that in response to the needle protection device 100 being in the shield position, opposing sides of each of the slits 142 are touching and that the tubular portion 124 is entirely closed. In this manner, some embodiments may limit exposure to any part of the needle 102, and to any associated blood spatter or residual blood.

As previously mentioned, in some embodiments, the first end 122a of the first arm 118a may be formed by a first pair of slits 142a,b extending through the distal end 138 of the tubular portion 124. In some embodiments, the slits 142a,b may be substantially identically formed and may be a same length and/or orientation as each other. As illustrated, for example, the first pair of slits 142a,b may extend in parallel along a length of the tubular portion 124, such that a first end 122a of the first arm 118a is disposed at less than a quarter of the length of the housing 116. Likewise, the first end 122b of the second arm 118b may be formed by a second pair of slits 142c,d extending through the distal end 138 of the tubular portion 124. In some embodiments, as each of the arms 118a,b may be formed from the tubular portion 124 itself, the first end 122a of the first arm 118a and the first end 122b of the second arm 118b may be generally planar and flush with an outer surface of the tubular portion 124 in response to the needle 102 being in the ready position.

As illustrated in FIGS. 3A-3D, in some embodiments, the hub 106 may include a distal end 108, a proximal end 110, and a lumen 112 extending through the distal end 108 and the proximal end 110. In some embodiments, the lumen 112 may include an inner diameter at least slightly larger than an outer diameter of the housing 116 such that the housing 116 may be disposed within the lumen 112. Further, in some embodiments, the housing 116 may include an inner diameter at least slightly larger than an outer diameter of the needle 102 to allow the needle 102 to slide therethrough.

In some embodiments, the needle 102 may be disposed within the hub 106 when the needle 102 is in the ready position for insertion into the vein of the patient. The ready position is illustrated in FIG. 3A, according to some embodiments. In some embodiments, the needle 102 may be movable between the ready position in which the sharp distal tip 104 is outside of the housing 116 and the hub 106, and a retracted position in which the sharp distal tip 104 is shielded within the housing 116 and lumen 112 of the hub 106. The retracted needle 102 position is illustrated in FIGS. 3C and 3D, according to some embodiments.

In some embodiments, in the ready position, the needle 102 may extend through the proximal end 140 and the distal end 138 of the tubular portion 124, thereby urging the arms 118 outwardly towards the hub 106. In some embodiments, the arms 118 may be substantially resilient such that the arms 118 may be biased against an elongated shaft 150 of the needle 102. In some embodiments, the bent portions 128a,b of each of the arms 118 may also be urged outwardly such that they protrude from an outer surface of the tubular portion 124.

In some embodiments, the first arm 118a may include a first interlock protrusion. In some embodiments, the first bent portion 128a may include or correspond to the first interlock protrusion and/or the second bent portion 128b may include or correspond to the second interlock protrusion. In some embodiments, the interlock protrusions may automatically secure and retain the housing 116 within the lumen 112 during operation of the needle 102.

As illustrated in FIG. 3A, in some embodiments, an inside surface or lumen 112 of the hub 106 may include one or more recesses, which may include grooves, windows, undercuts, indents, or other features to automatically interlock with the bent portions 128a,b or other such interlock protrusions, thereby facilitating automatic retention of the housing 116 within the hub 106 during use. Additionally, the interlock protrusions may be integrated with or coupled to the duckbill valve 136 such the needle protection device 100 may not be accidentally or intentionally removed before the sharp distal tip 104 of the needle 102 is retracted and secured within the housing 116. In some embodiments, as long as the needle 102 is extended through the housing 116 such that the arms 118 are biased against the elongated shaft of the needle 102, the interlock protrusions may automatically secure the housing 116 within the hub 106 and prevent the needle protection device 100 from being inadvertently or intentionally removed. In some embodiments, the inside surface or lumen 112 of the hub 106 may include the recesses or an annular groove, the interlock protrusions may be disposed within the recesses or the annular groove in response to the needle 102 being in the ready position.

In some embodiments, in response to withdrawing the needle 102 in a proximal direction beyond the second end 126a of the first arm 118a and the second end 126b of the second arm 118b, the arms 118 may relax, causing the duckbill valve 136 to close. In some embodiments, the interlock protrusions may in turn disengage from the recesses or other interlocking features of the lumen 112, thereby facilitating removal of the housing 116 from the hub 106. In some embodiments, features of the needle protection device 100 positioned at or near a proximal end 140 of the tubular portion 124 may maintain the sharp distal tip 104 of the needle 102 securely within the housing 116 upon removal of the housing 116 from the hub 106.

In some embodiments, withdrawal of the needle 102 in the proximal direction may actuate the needle protection device 100 to secure the sharp distal tip 104 of the needle 102. Specifically, withdrawing the sharp distal tip 104 of the needle 102 in the proximal direction beyond the second end 126a of the first arm 118a and the second end 126b of the second arm 118b may cause the arms 118, which may be resilient, to snap closed, thus closing the duckbill valve 136.

In some embodiments, the needle 102 may include a notch 154 providing access to an inner lumen of the needle 102. In operation, the notch 154 may enable observation of blood flashback upon entry of the sharp distal tip 104 into a patient's vasculature. In some embodiments, withdrawing the needle 102 in the proximal direction such that the duckbill valve 136 closes, may dispose the notch 154 within the tubular portion 124. In this manner, the sharp distal tip 104 may be prevented from movement in a distal direction beyond the duckbill valve 136, thereby preventing re-exposure to the sharp distal tip 104 and any blood that may be released from the sharp distal tip 104 and/or the notch 154.

As illustrated in FIG. 3D, the needle 102 in accordance with some embodiments may include a needle feature 152 such as a bump, crimp, protrusion or another suitable feature disposed near a distal end of the needle 102. In some embodiments, the needle feature 152 may be located proximate to the notch 154. In some embodiments, the needle feature 152 may include a diameter larger than a diameter of an opening of a proximal end 141 of the housing 116. In some embodiments, as discussed in more detail below, the proximal end 141 of the housing 116 may include a washer, which may have a diameter less than the diameter of the needle feature 152. Withdrawing the needle 102 in the proximal direction may force the needle feature 152 against the proximal end 141 of the housing 116 or washer, thereby precluding the sharp distal tip 104 and notch 154 from exiting the needle protection device 100.

Figure 4A:
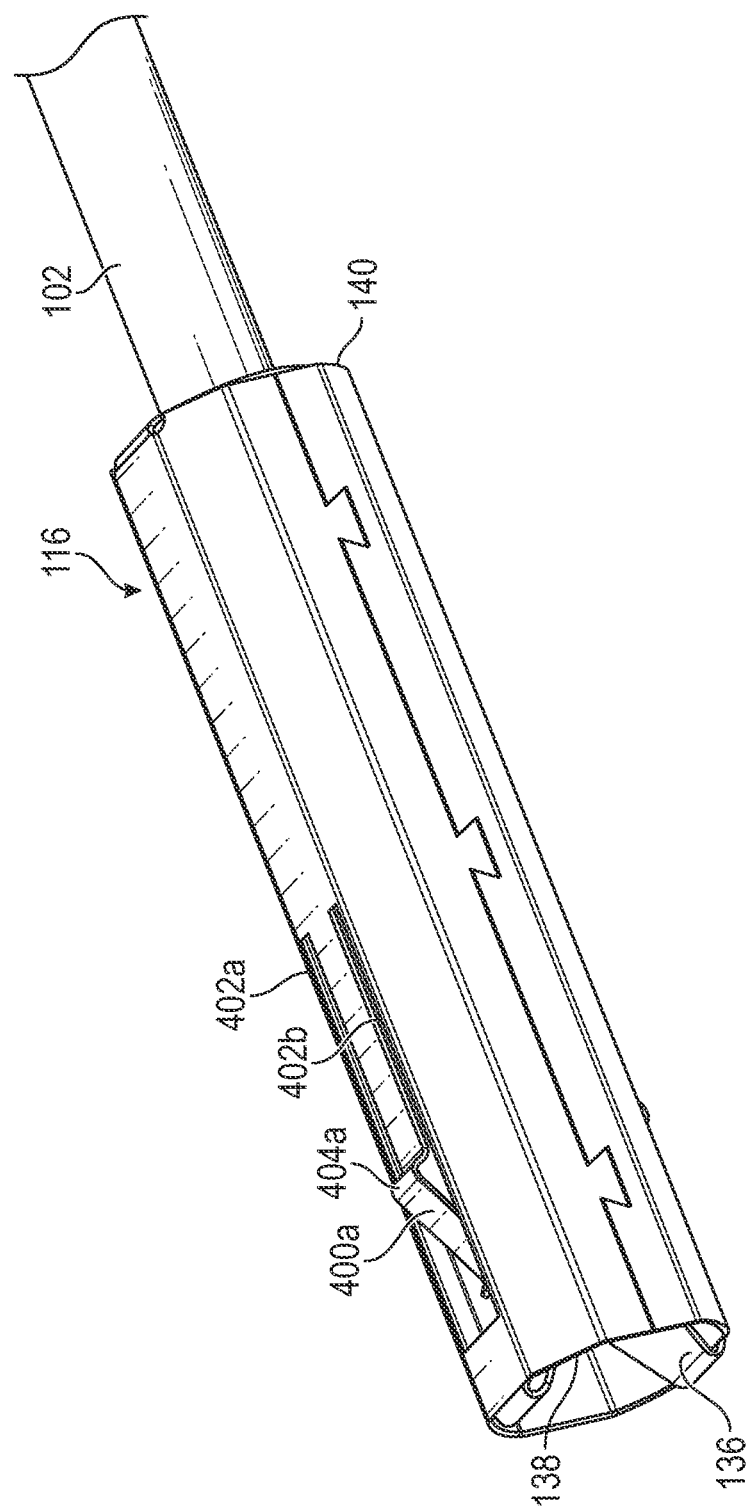
FIG. 4A is an upper perspective view of another example needle protection device, in accordance with some embodiments.
Figure 4B:
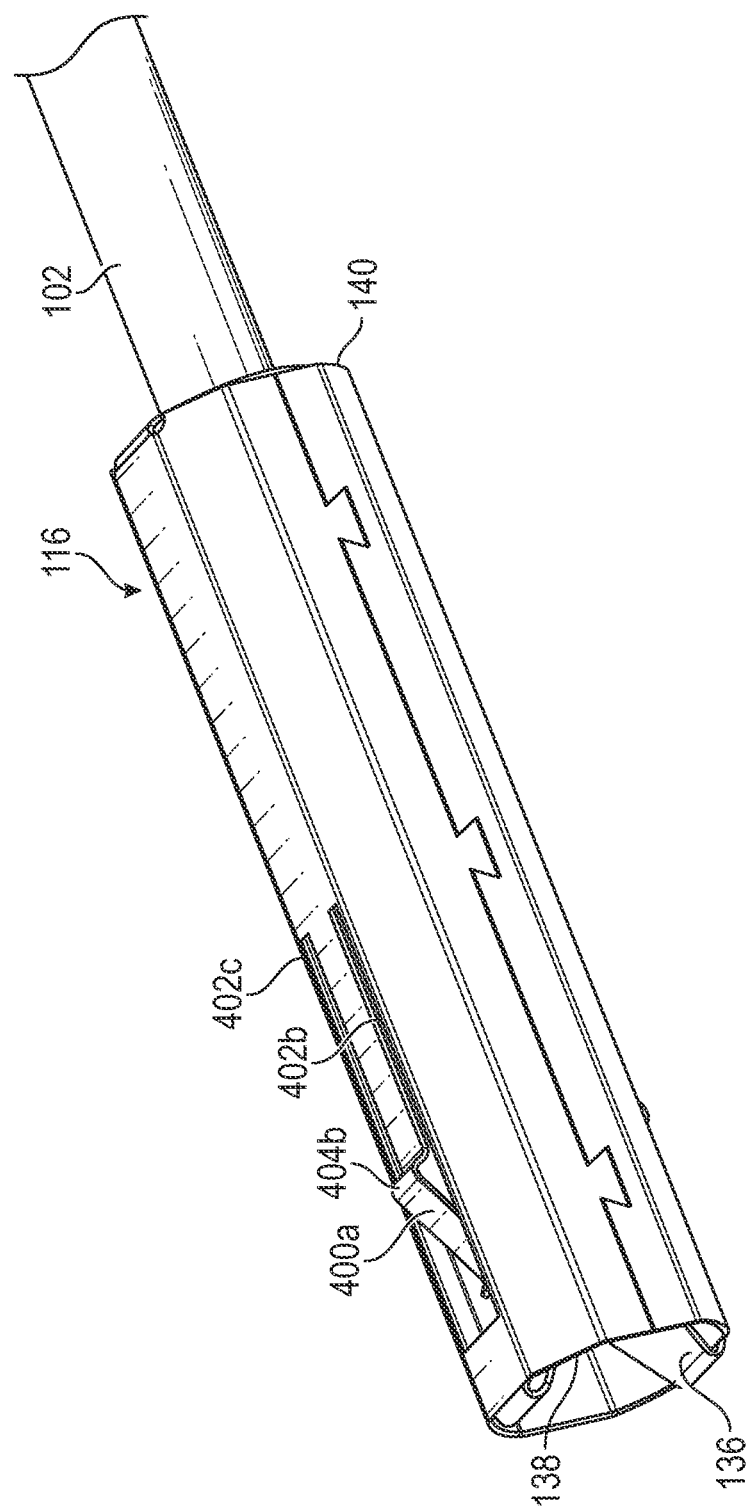
FIG. 4B is a lower perspective view of the needle protection device of FIG. 4A, in accordance with some embodiments.
Figure 4C:
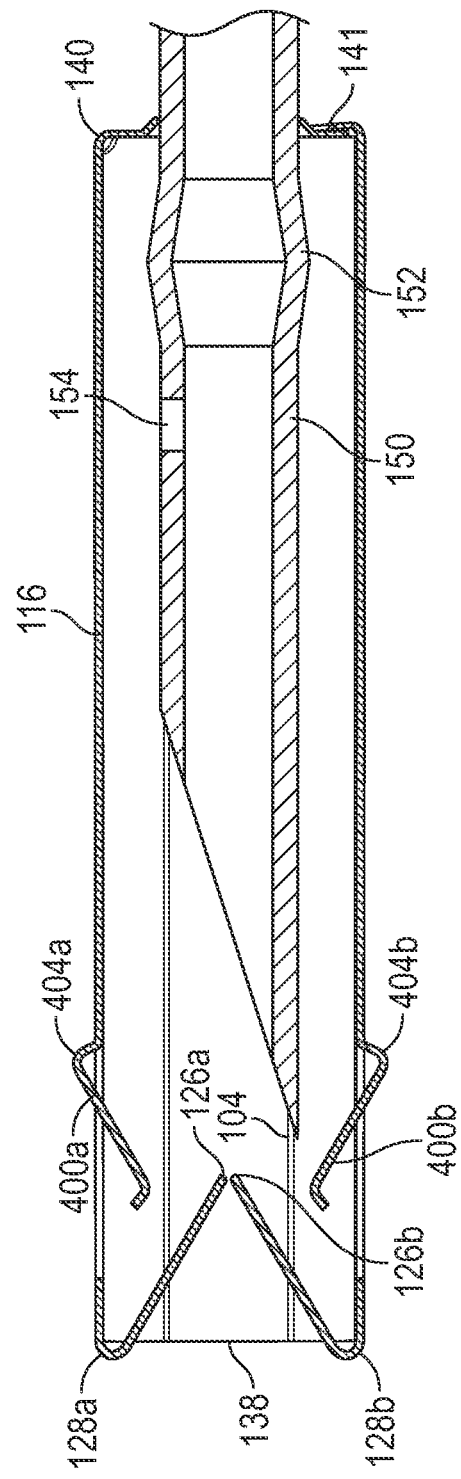
FIG. 4C is a cross-sectional view of the needle protection device of FIG. 4A, in accordance with some embodiments.

Referring now to FIGS. 4A-4C, in some embodiments, the needle protection device 100 may include a first spring element 400a and/or a second spring element 400b to create a biasing force against the second ends 126a,b of the arms 118. The first spring element 400a and the second spring element 400b may be referred to herein as "spring elements 400." In some embodiments, the first spring element 400a may be formed from a pair of slits 402a,b formed within the tubular portion 124. In some embodiments, the second spring element 400b may be formed from a pair of slits 402c,d formed within the tubular portion 124. In some embodiments, narrow sections formed between the pair of slits 402a,b may be urged outwardly from the tubular portion 124 and bent or otherwise molded or deformed to form the spring elements 400a,b configured to store potential energy.

In some embodiments, in response to the needle 102 extending through the tubular portion 124 and the duckbill valve 136, the arms 118 may be urged outwardly towards the hub 106 such that the first spring element 400a may contact the second end 126a of the first arm 118a and the second spring element 400b may contact the second end 126b of the second arm 118b. In some embodiments, the first spring element 400a may exert a perpendicular or transverse force against the second end 126a of the first arm 118a relative to the tubular portion 124. Similarly, in some embodiments, the second spring element 400b may exert a perpendicular or transverse force against the second end 126b of the second arm 118b in a direction substantially opposite the force exerted by the first spring element 400a. In some embodiments, in response to withdrawal of the sharp distal tip 104 of the needle 102 beyond the second ends 126a,b of the arms 118, the perpendicular or transverse forces may urge the second ends 126a,b of the arms 118 towards each other. This may thereby create an effective and reliable mechanism to automatically close the duckbill valve 136 and prevent re-exposure of the sharp distal tip 104.

In some embodiments, the first spring element 400a and/or the second spring element 400b may also provide an interlock mechanism to secure the housing 116 within the hub 106. In some embodiments, the first spring element 400a and the second spring element 400b may include the interlock protrusions, which may include the bent portions 128. In some embodiments, the bent portions 128 may be disposed within one or more of the recesses of the hub 106 in response to the needle 102 being in the ready position. In some embodiments, the spring elements 400 may protrude outwardly from the housing 116 when the needle 102 is extended within the housing 116.

Specifically, in some embodiments, the elongated shaft 150 of the needle 102 may urge each of the arms 118 outwardly towards the hub 106, such that the spring elements 400a,b contact the second ends 126 of each of the arms 118. In some embodiments, each of the spring elements 400a,b may include a respective bent portion 404a,b to store potential energy. When the needle 102 forces the arms 118 and corresponding spring elements 400a,b outwardly towards the hub 106, the bent portions 404a,b may also be forced outwardly towards the hub 106 such that they protrude from an outer surface of the tubular portion 124. In some embodiments, such bent portion 404a,b may interlock with the recesses or other features integrated into or coupled to an inner wall of the hub 106, thereby retaining the housing 116 within the hub 106.

Withdrawing the needle 102 from the housing 116 may relax the arms 118 within the tubular portion 124, causing an end of each of the spring elements 400a,b to extend through a corresponding slit or aperture in the housing 116. The bent portions 404a,b of each of the spring elements 400a,b may also relax, thereby disengaging the recesses or other features of the hub 106. This may facilitate removal of the housing 116 from the hub 106.

Figure 5A:
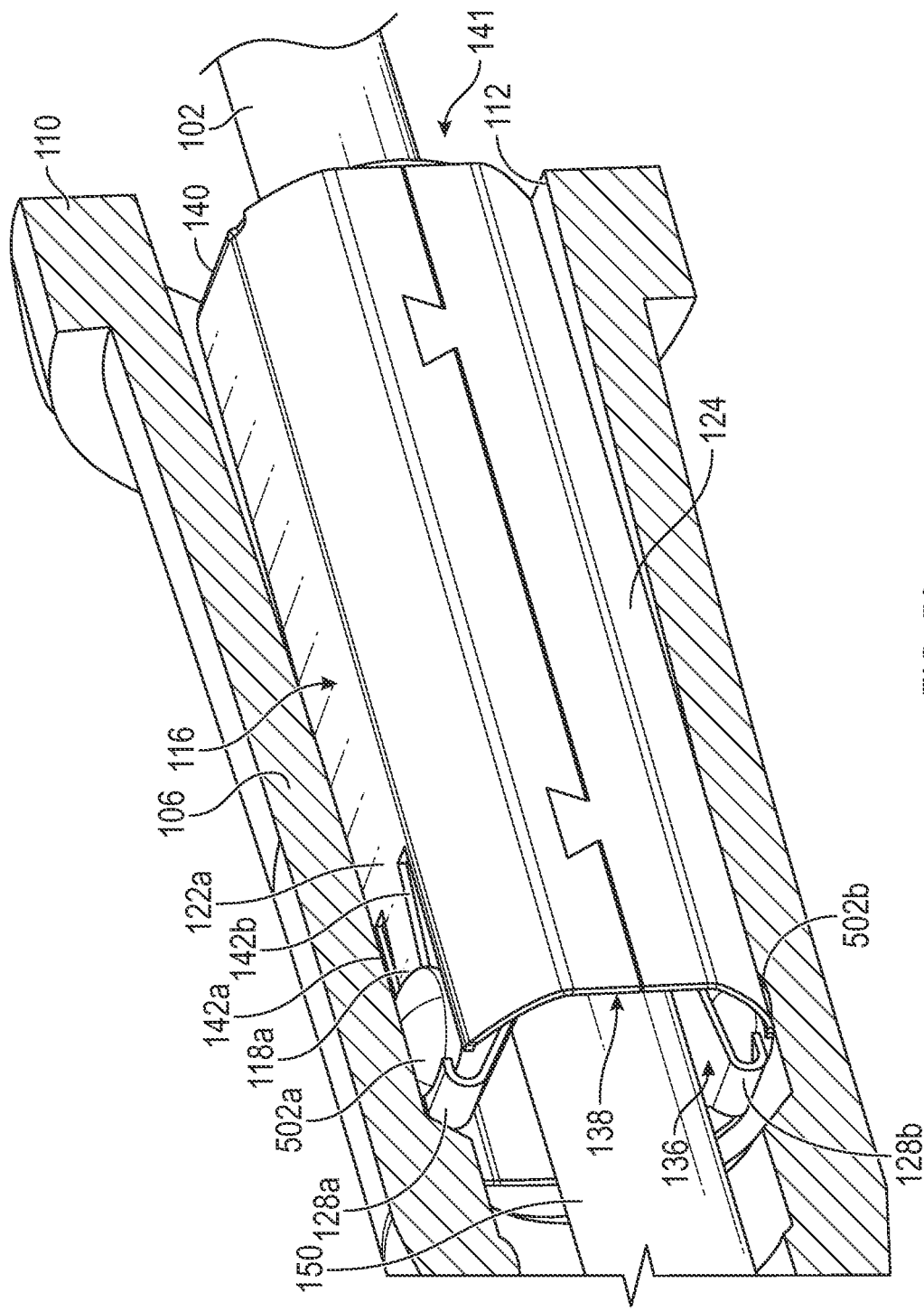
FIG. 5A is a partial cutaway view of an example access system, illustrating the needle in the ready position and another example needle protection device including friction pads, in accordance with some embodiments.
Figure 5B:
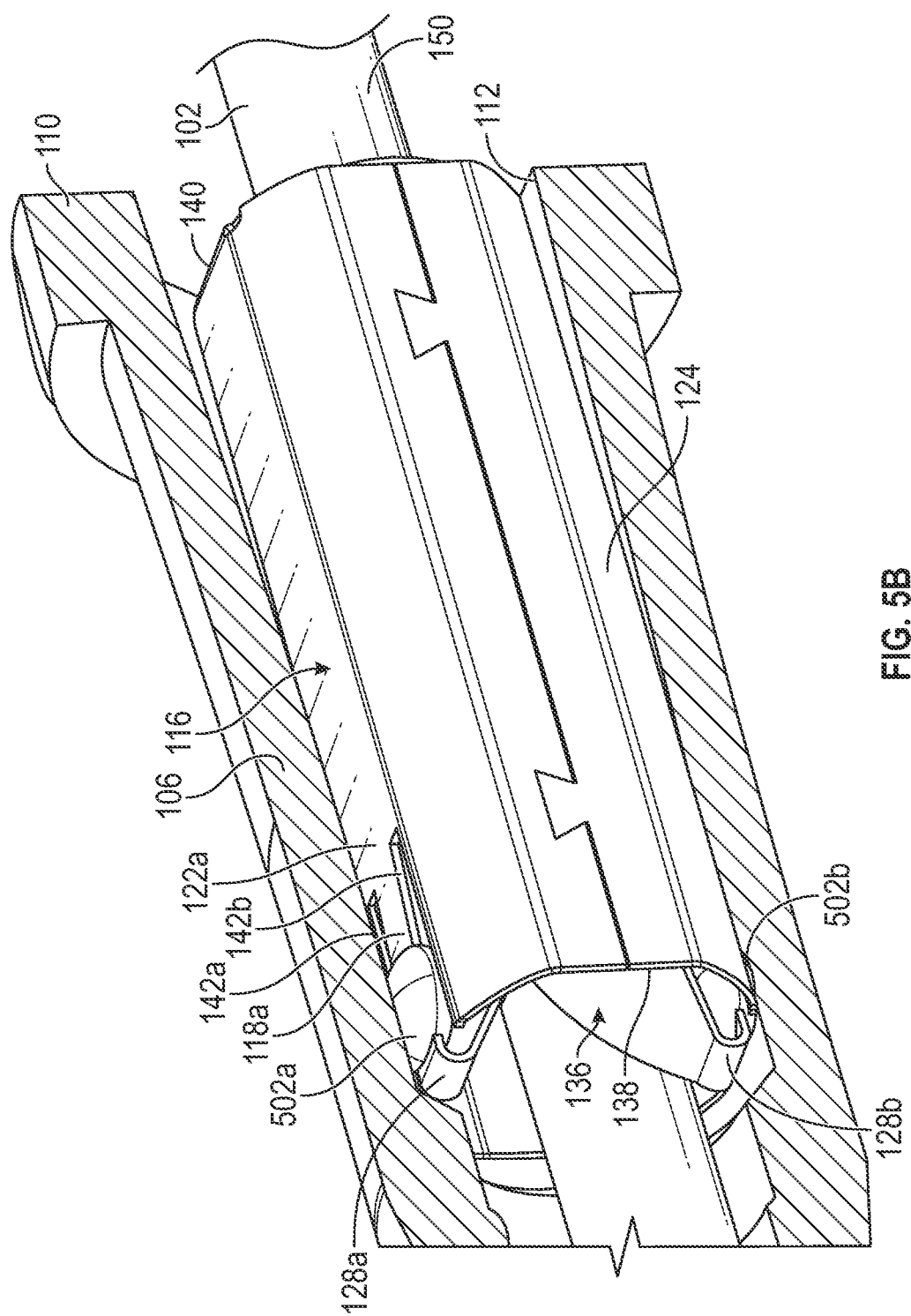
FIG. 5B is a partial cutaway view of the access system of FIG. 5A, illustrating the needle in the shielded position, in accordance with some embodiments.
Figure 6A:
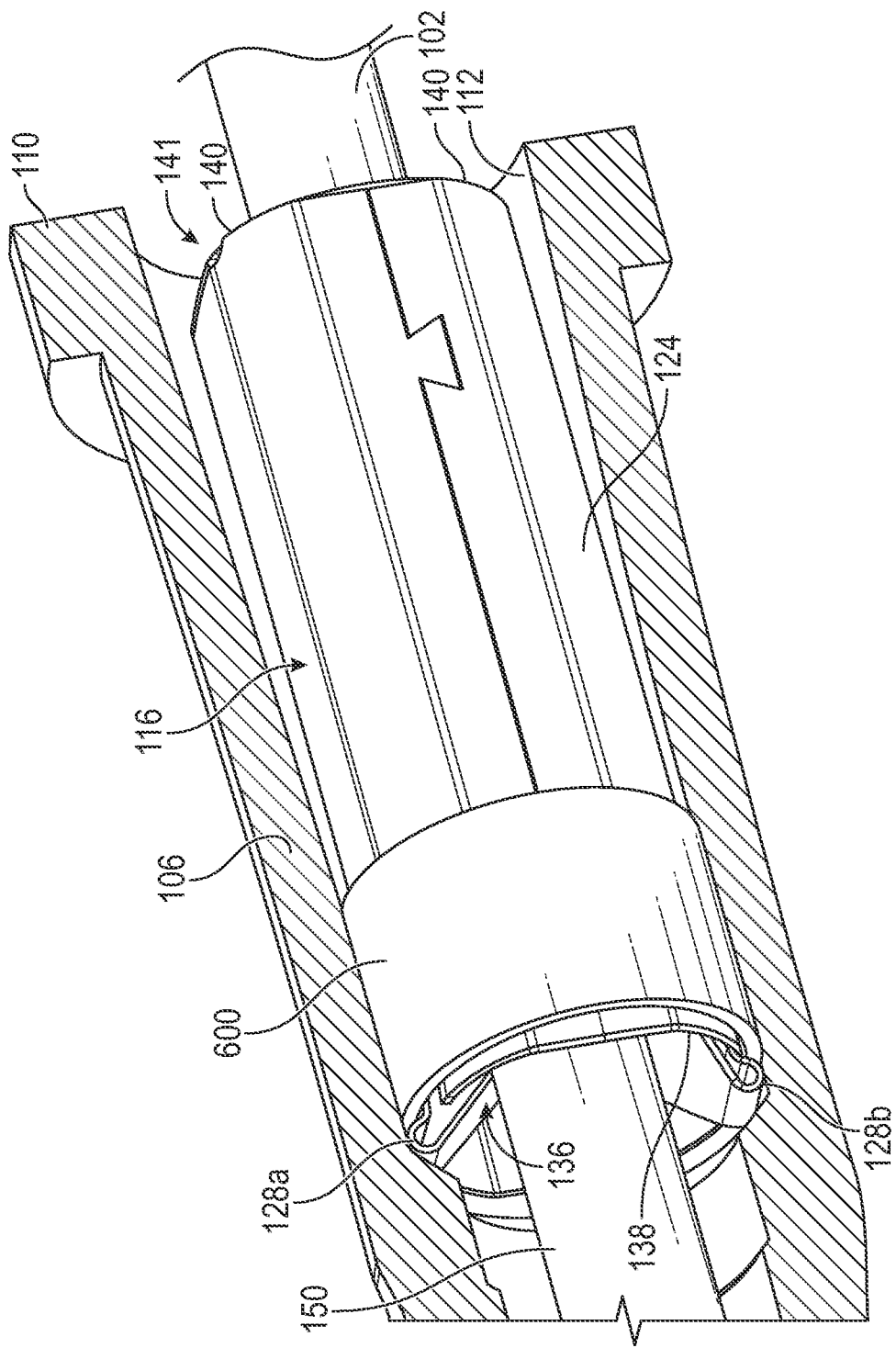
FIG. 6A is a partial cutaway view of another access system, illustrating the needle in the ready position and another example needle protection device including a friction band, in accordance with some embodiments.
Figure 6B:
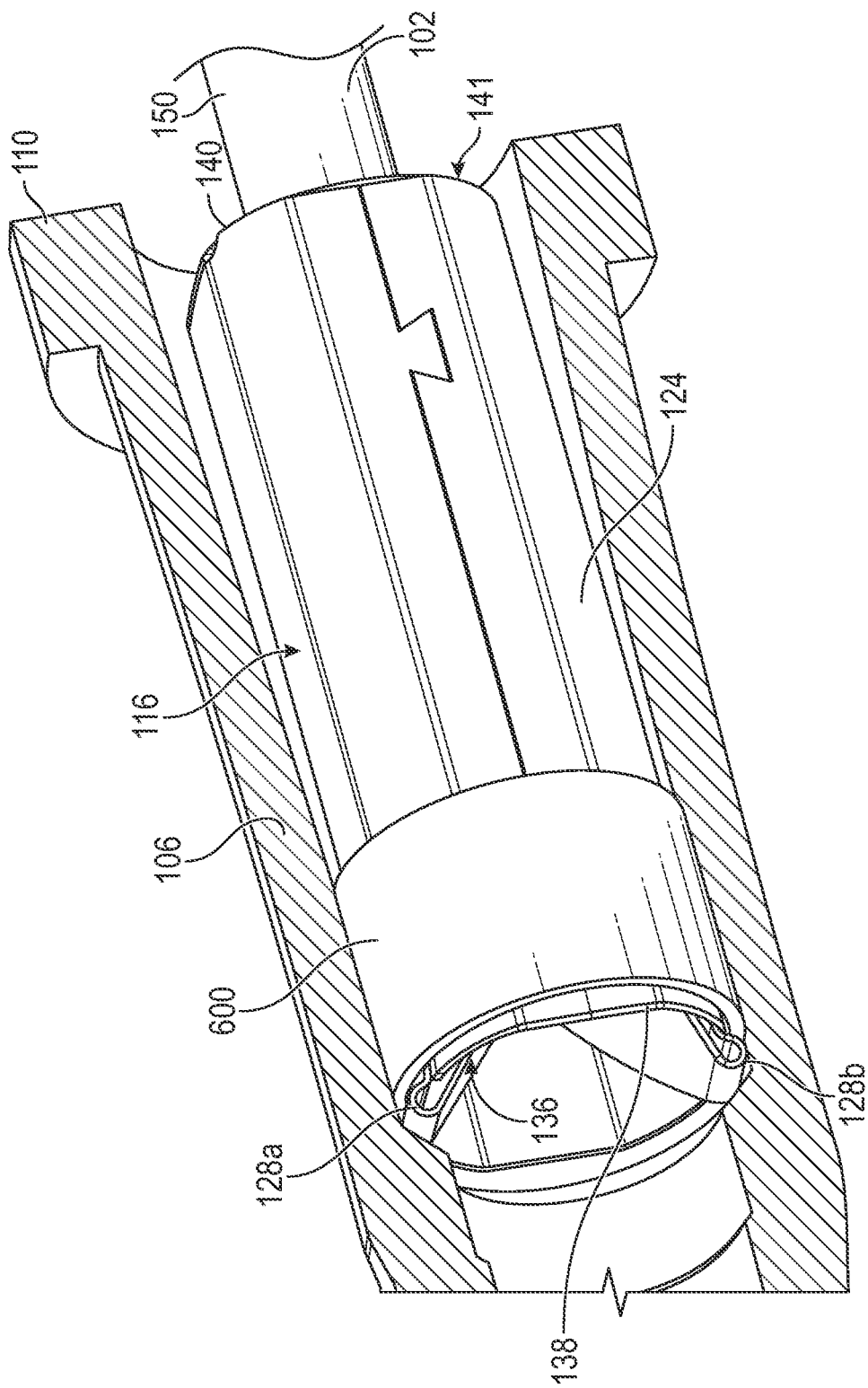
FIG. 6B is a partial cutaway view of the access system of FIG. 6A, illustrating the needle in the shielded position, in accordance with some embodiments.

Referring now to FIGS. 5 and 6, in other embodiments, the needle protection device 100 may include one or more retention features or friction components to secure the housing 116 within the hub 106 while the needle 102 is extended therethrough during use. In some embodiments, a particular retention feature or friction component may include a friction pad (such as friction pads 502a,b), a friction band 600, a friction enclosure, or another suitable retention feature. The retention features may be integrated with or coupled to the housing 116 to increase friction between an exterior surface of the housing 116 and an interior surface of the hub 106, thereby securing the housing 116 within the hub 106.

As illustrated in FIG. 5, in some embodiments, one or more friction pads 502a,b may be integrated with or coupled to the first arm 118a and/or the second arm 118b, extending from the tubular portion 124 of the housing 116. As illustrated, in some embodiments, a friction pad 502a may be coupled to the first end 122a of the first arm 118a near the distal end 138 of the tubular portion 124. In some embodiments, in response to the elongated shaft 150 of the needle 102 forcing the second end 126a of the first arm 118a outwardly toward the inner surface of the hub 106, the first end 122b of the first arm 118a may also be forced outwardly toward the hub 106. In this manner, the friction pad 502a,b may also be forced outwardly to contact the inner surface or lumen 112 of the hub 106.

In some embodiments, the friction pads 502a,b may include a rounded or elevated contour such that, although the arm 118 may lie substantially flush with an outer surface of the housing 116, the friction pad 502a may protrude therefrom. In this manner, the friction pads 502a,b may contact and interact with an inner surface or lumen 112 of the hub 106 to secure the housing 116 within the hub 106 when the needle 102 is extended within the housing 116.

In some embodiments, the friction pads 502a,b may include a resilient material, such as rubber or plastic or another suitable material, to resist movement of the housing 116 relative to the inner surface or lumen 112 of the hub 106. In some embodiments, the friction pads 502a,b may include an outer surface 504, which may be textured to increase friction between the outer surface 504 of the friction pads 502a,b and the inner surface or lumen 112 of the hub 106. In some embodiments, the inner surface or lumen 112 of the hub 106 may also include textural features such as bumps, recesses, ripples, indentations, ridges, lines, or the like to increase friction between the lumen 112 and the friction pads 502a,b.

Referring now to FIG. 6, in some embodiments, the retention feature may include a friction band 600 or enclosure applied to a perimeter of the housing 116 near its distal end 138. The friction band 600 or enclosure may include a flexible and/or resilient material such as a rubber, plastic, or another suitable material. In some embodiments, the material may be a thin, sheet-like material, which may include dimensions configured to circumscribe at least a portion of the tubular portion 124. In some embodiments, a bottom side of the friction band 600 or enclosure may be disposed adjacent to an outer surface of the tubular portion 124, while a top side of the friction band 600 or enclosure may mediate contact between the tubular portion 124 and the inner surface or lumen 112 of the hub 106. In some embodiments, either or both of the top side and the bottom side may be textured to increase friction and resistance between the friction band 600 and the adjacent surface. In this manner, the friction band 600 may secure the housing 116 in the hub 106.

In some embodiments, the friction band 600 may be forced outwardly by the arms 118 of the housing 116 in response to the elongated shaft 150 of the needle 102 being extended through the housing 116 in a ready position. This increased pressure in an outward direction against the friction band 600 may increase resistance between the friction band 600 and the hub 106 lumen 112, thereby further securing the housing 116 within the hub 106.

Withdrawing the sharp distal tip 104 of the needle 102 beyond the second ends 126 of each of the arms 118 may cause the first ends 122 of the arms 118 to relax. This may cause the friction band 600 to relax and, in some embodiments, to contract against the perimeter of the tubular portion 124. Resistance between the friction band 600 and the lumen 112 may be reduced, and the housing 116 may be spaced apart from the hub 106. This may facilitate removal of the housing 116 from the hub 106.

In some embodiments, the friction band 600 may include a sleeve or enclosure substantially enclosing the distal end 138 of the housing 116. Further, in some embodiments, the sleeve may include an opening or aperture at its distal end to accommodate the needle 102 therethrough in the event the needle 102 is extended through the housing 116 for use. In some embodiments, the opening or aperture may be substantially elastic such that it automatically closes upon withdrawal of the needle 102 therethrough.

Figure 7A:
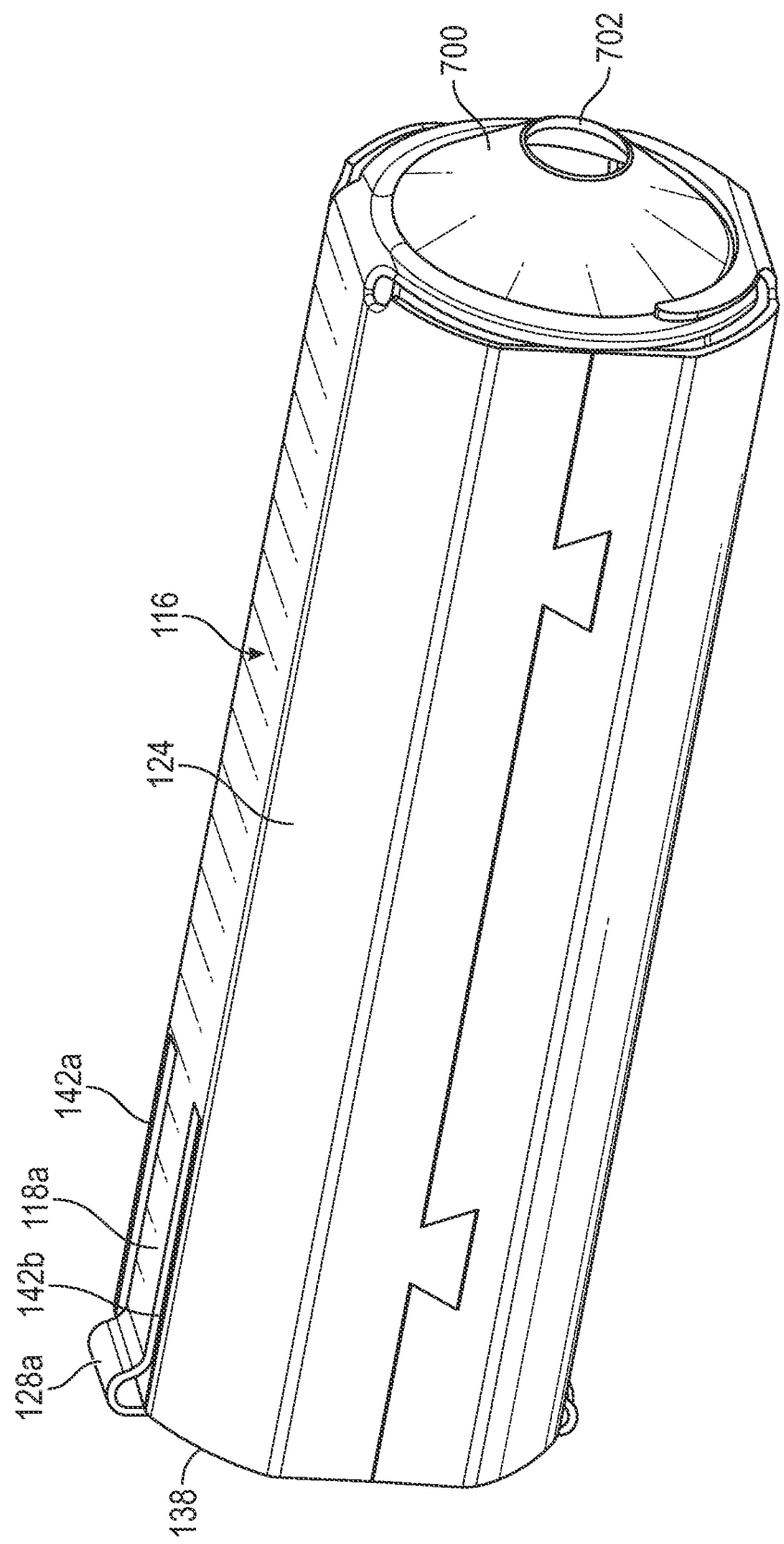
FIG. 7A is an upper perspective view of another example needle protection device including a washer at its proximal end, in accordance with some embodiments.
Figure 7B:
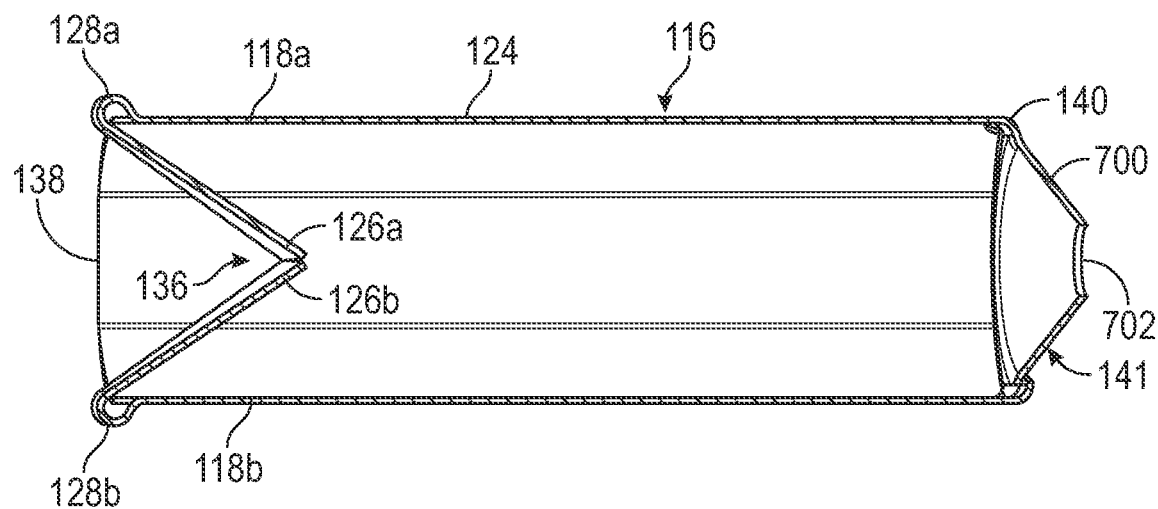
FIG. 7B is a cross-sectional view of the example needle protection device of FIG. 7A, in accordance with some embodiments.

Referring now to FIGS. 7A and 7B, in some embodiments, the proximal end 141 of the housing 116 may include the washer 700. In some embodiments, the washer 700 may be coupled to the proximal end of the tubular portion 124. For example, the washer 700 may be attached to the proximal end of the tubular portion 124 or monolithically formed with the tubular portion 124 as a single unit. In some embodiments, the washer 700 may be resilient and/or may include an opening 702 to enable the needle 102 (see, for example, FIGS. 2A-3D) disposed within the housing 116 to slide with respect thereto. In some embodiments, the opening 702 may be circular or another suitable opening. In some embodiments, the opening 702 may include a diameter or dimensions smaller than a diameter or dimensions of a bump, crimp, or other needle feature 152 located proximate to the sharp distal tip 104 of the needle 102. As discussed above, the needle feature 152 may be located proximal to the notch 154 providing access to the lumen 112 of the needle 102. In some embodiments, withdrawing the sharp distal tip 104 of the needle 102 in the proximal direction may cause the needle feature 152 to interfere with the opening 702, thereby precluding withdrawal of the sharp distal tip 104 and notch 154, and preventing re-exposure to residual blood and blood-borne pathogens that may be present.

All examples and conditional language recited herein are intended for pedagogical objects to aid the reader in understanding the described embodiments and the concepts contributed by the inventor to furthering the art and are to be construed as being without limitation to such specifically recited examples and conditions. Although some embodiments have been described in detail, it should be understood that the various changes, substitutions, and alterations could be made hereto without departing from the spirit and scope of various embodiments.

We claim:

1. An access system, comprising:
a hub, comprising a distal end, a proximal end, a lumen extending through the distal end and the proximal end;
a needle protection device to shield a sharp distal tip of a needle, the needle protection device comprising:
a housing disposed within the lumen of the hub, wherein the housing comprises a tubular portion, a first arm, and a second arm, wherein the first arm comprises a first end coupled to the tubular portion, a second end disposed within the tubular portion, and a first bent portion disposed between the first end of the first arm and the second end of the first arm, wherein the second arm comprises a first end coupled to the tubular portion, a second end disposed within the tubular portion, and a second bent portion disposed between the first end of the second arm and the second end of the second arm, wherein the second end of the first arm and the second end of the second arm form a duckbill valve, wherein the first bent portion and the second bent portion protrude further outwardly from a longitudinal axis of the housing than the tubular portion when the duckbill valve is closed and are proximate the second end of the first arm and the second end of the second arm forming the duckbill valve; and
a needle, comprising a sharp distal tip, wherein the needle extends through the housing and biases the first arm and the second arm outwardly towards the hub to facilitate retention of the housing within the hub, wherein in response to the sharp distal tip being withdrawn in a proximal direction beyond the second end of the first arm and the second end of the second arm, the duckbill valve closes and the first arm and the second arm move inwardly to facilitate removal of the housing from the hub,
wherein the tubular portion comprises a distal end and a proximal end, wherein the first end of the first arm is formed by a first slit and a second slit within the tubular portion, wherein the first end of the second arm is formed by a third slit and a fourth slit within the tubular portion, wherein the first slit, the second slit, the third slit, and the fourth slit extend through the distal end of the tubular portion, wherein the first slit, the second slit, the third slit, and the fourth slit extend along a portion of an entire length of the tubular portion such that proximal ends of the first slit, the second slit, the third slit, and the fourth slit are spaced apart from the proximal end of the tubular portion.

2. The access system of claim 1, wherein the tubular portion is closed except for a portion of the housing between the first slit and the second slit that comprises the first arm and another portion of the housing between the third slit and the fourth slit that comprises the second arm.

3. The access system of claim 1, wherein the needle comprises a feature disposed proximal to the sharp distal tip, wherein the housing comprises a proximal opening, wherein a diameter of the proximal opening is less than a diameter of the feature such that the sharp distal tip is prevented from being withdrawn proximally through the proximal opening.

4. The access system of claim 3, further comprising a washer coupled to a proximal end of the tubular portion, wherein the washer comprises the proximal opening.

5. The access system of claim 4, wherein the needle further comprises a notch providing access to a lumen of the needle, wherein in response to the sharp distal tip being withdrawn in the proximal direction beyond the second end of the first arm and the second end of the second arm and the feature contacting the washer, the notch is disposed within the tubular portion proximal to the duckbill valve.

6. The access system of claim 1, wherein the hub further comprises an inner surface forming the lumen, wherein the inner surface comprises a recess wherein the first arm comprises a first interlock protrusion and the second arm comprises a second interlock protrusion, wherein in response to the needle extending through the duckbill valve, the first interlock protrusion and the second interlock protrusion are disposed within the recess to facilitate retention of the housing within the hub, wherein in response to the sharp distal tip being withdrawn in the proximal direction beyond the second end of the first arm and the second end of the second arm, the duckbill valve closes and the first interlock protrusion and the second interlock protrusion are removed from the recess to facilitate removal of the housing from the hub.

7. The access system of claim 6, wherein the first bent portion comprises the first interlock protrusion, and the second bent portion comprises the second interlock protrusion.

8. The access system of claim 6, wherein the first interlock protrusion is disposed proximal to the first bent portion, wherein the second interlock protrusion is disposed proximal to the second bent portion.

9. The access system of claim 1, further comprising a friction pad coupled to the first arm, wherein the needle extends through the housing and biases the first arm outwardly towards the hub such that the friction pad contacts the hub.

10. The access system of claim 9, further comprising another friction pad coupled to the second arm, wherein the needle extends through the housing and biases the second arm outwardly towards the hub such that the another friction pad contacts the hub.

11. The access system of claim 10, wherein in response to the sharp distal tip being withdrawn in the proximal direction beyond the second end of the first arm and the second end of the second arm, the first friction pad and the another friction pad are spaced apart from the hub.

12. The access system of claim 1, further comprising a friction band surrounding the housing, wherein the needle extends through the housing and biases the first arm and the second arm outwardly towards the hub such that the friction band contacts the hub.

13. The access system of claim 12, wherein in response to the sharp distal tip being withdrawn in the proximal direction beyond the second end of the first arm and the second end of the second arm, the friction band is spaced apart from the hub.

14. The access system of claim 1, wherein the first end of the first arm and the first end of the second arm are generally planar and flush with an outer surface of the tubular portion.

15. The access system of claim 1, wherein the housing is monolithically formed as a single unit.

* * * * *